United States Patent [19]
Smith et al.

[11] 4,154,093
[45] May 15, 1979

[54] MEASUREMENT OF VISCOELASTIC PROPERTIES

[75] Inventors: Norman D. P. Smith, Farnham; Thomas A. Wright, Hedgerley, both of England

[73] Assignee: Imperial Chemical Industries Limited, London, England

[21] Appl. No.: 893,834

[22] Filed: Apr. 6, 1978

[30] Foreign Application Priority Data

Apr. 12, 1977 [GB] United Kingdom ............... 15028/77

[51] Int. Cl.² .......................................... G01N 11/16
[52] U.S. Cl. ...................................................... 73/54
[58] Field of Search ................... 73/59, 60, 54, 64.1

[56] References Cited

U.S. PATENT DOCUMENTS 3,181,348  5/1965  Lewis .................................. 73/59 X

FOREIGN PATENT DOCUMENTS 810242  3/1959  United Kingdom ....................... 73/59

Primary Examiner—Charles A. Ruehl
Assistant Examiner—Joseph W. Roskos
Attorney, Agent, or Firm—Cushman, Darby & Cushman

[57] ABSTRACT

A method and apparatus for measuring the viscoelastic characteristics of a sample of a viscous liquid or gel contained within a closed can or other cylindrical vessel. The can and sample are subjected to torsional oscillation about a vertical axis by an oscillation source through an elastic coupling member, the oscillation source operating either (i) at a fixed, predetermined frequency or (ii) at the resonant frequency of the can and sample. Measurements are made of the amplitude of oscillation of the can and sample and of either (i) the angular phase difference between the oscillation of the can and sample and those of the source or (ii) the resonant frequency of the can and sample. The measured data may be used either to compare the sample with a standard material or to calculate viscoelastic moduli of the sample.

9 Claims, 4 Drawing Figures

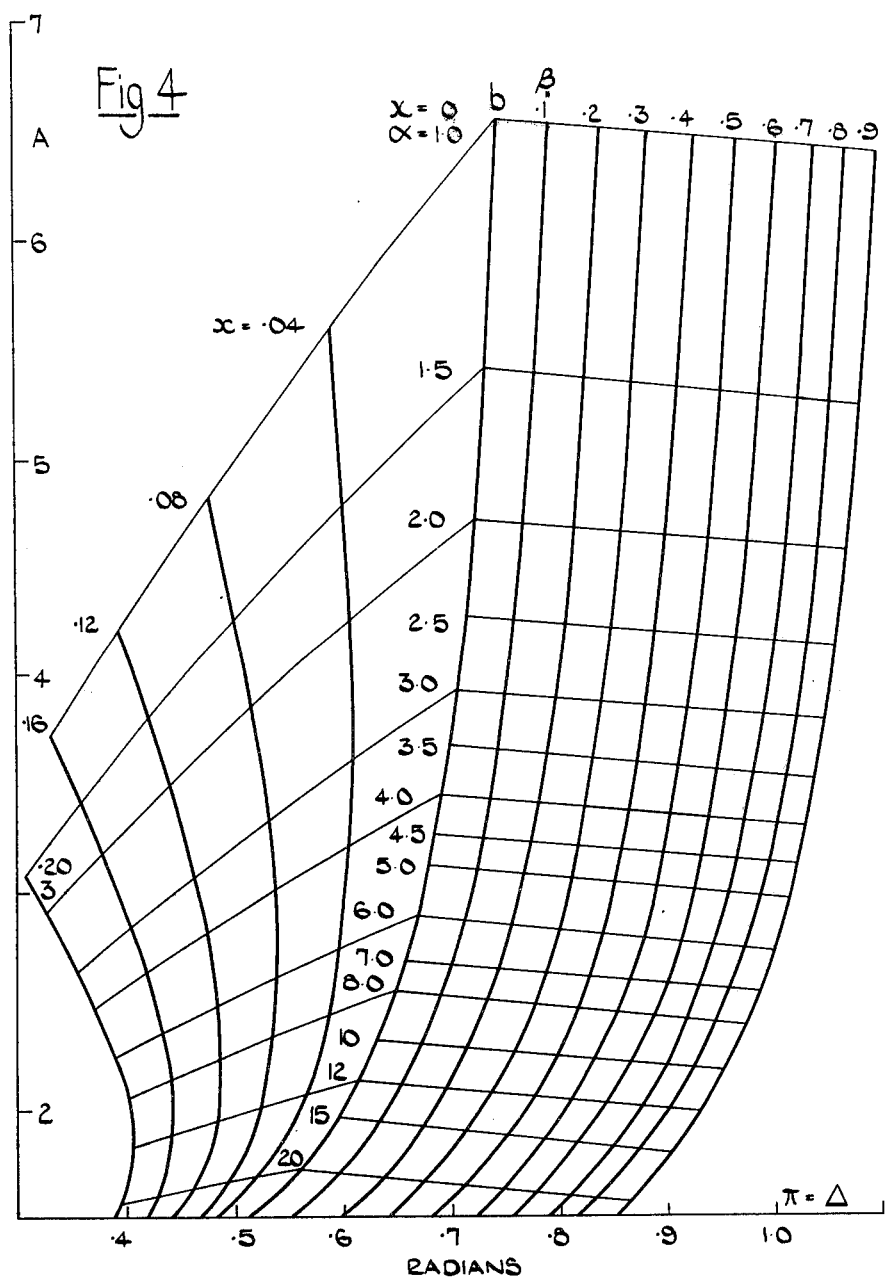

MEASUREMENT OF VISCOELASTIC PROPERTIES

This invention relates to the measurement of the viscoelastic characteristics of viscous liquids, gels and like materials, in particular to a method of measuring such characteristics on a sample of the material contained within a vessel of specified shape. The invention also relates to an apparatus suitable for carrying out the method. The term "viscous liquid-like" is used in the present specification and claims means viscous liquids, gels and materials of intermediate state between a viscous liquid and a gel.

Methods of measuring the viscoelastic moduli of viscous liquids, gels and other materials of a state intermediate between viscous liquids and gels, have previously been proposed in which the material to be studied is subjected to an oscillatory stress or strain and the resultant strain or stress respectively is determined; the viscoelastic moduli can be calculated from the observed values by known procedures. Methods have also been proposed of measuring the viscosity of a liquid contained within a hollow spherical or cylindrical vessel, in which the vessel is supported symmetrically about its vertical axis and torsional oscillations about that axis are induced in it; the viscosity can be deduced from measurements of the rate of decay of the oscillations. Further, a variant of this last-mentioned method has been proposed in which a torsional pulse is applied to the vessel each time the latter passes through the mid-position of oscillation, in such a way that an oscillation of steady amplitude is generated; measurement of this steady amplitude enables the viscosity of the liquid to be calculated.

The foregoing methods have not, however, been proposed for use under routine conditions and, in particular, the equipment that has been developed for performing the methods has not been of a suitable type to satisfy the need for rapid, non-destructive testing of the viscoelastic properties of liquids and like materials when contained within either sealed or unsealed vessels, under typical industrial conditions.

The present invention provides a method and apparatus for conveniently making rapid measurements of viscoelastic characteristics upon liquids, gels and materials of intermediate state when the latter are contained within vessels of cylindrical or other axially symmetrical shape of circular cross-section. The characteristics measured may be used directly as a basis for the empirical comparison of samples; alternatively the viscoelastic moduli of the material under test, or parameters related to those moduli, can be obtained either by calculation according to certain theoretical formulae or by reference to calibration graphs or tables previously prepared by calculation using such formulae.

Thus according to the present invention there is provided a method of measuring viscoelastic characteristics of a sample of a viscous liquid, a gel or a material of intermediate state between a viscous liquid and a gel (hereinafter referred to as a "liquid") whilst the sample is contained within a hollow vessel the walls of which describe a solid of revolution about the axis of symmetry of the vessel, the method comprising:

(a) supporting the vessel and sample and subjecting them to torsional oscillation about a vertical axis coinciding with the axis of symmetry of the vessel, the torsional oscillation being imparted to the vessel through an elastic coupling by a source of oscillation which is either of fixed, predetermined frequency or is adjusted to the resonant frequency of the vessel, its support and the sample in conjunction with the elastic coupling;

(b) measuring the amplitude of the resulting oscillation of the vessel and also measuring either (i) the angular phase difference between the oscillations of the vessel and those of the source, in the case where the source operates at a fixed, predetermined frequency, or (ii) the resonant frequency of the vessel and sample, in the case where the source is adjusted to that frequency; and (c) comparing the measured values for the sample with the corresponding known values for a standard liquid, or deriving viscoelastic moduli, or parameters related thereto, from the measured values for the sample by means of mathematical formulae or by means of calibration graphs or tables prepared with the aid of such formulae.

The invention also provides an apparatus suitable for the measurement of the viscoelastic characteristics of a sample of liquid as hereinbefore defined, which sample is contained within a hollow vessel the walls of which describe a solid of revolution about the axis of symmetry of the vessel, the apparatus comprising the following components:

(1) means for supporting the vessel so that its axis of symmetry is vertical, the said means being mounted for low-friction oscillation about a vertical axis passing through its centre but being constrained from moving in any other mode;

(2) means attached to the supporting means for locating thereupon a vessel as hereinbefore defined containing the sample of liquid so that the axis of symmetry of the vessel coincides with the vertical axis of the supporting means and so that the vessel does not move relatively to the supporting means during oscillation thereof;

(3) means for generating a mechanical oscillation of either fixed, predetermined frequency or of adjustable frequency;

(4) means for elastically coupling the supporting means to the oscillation-generating means so that the supporting means is subjected in response thereto to a torsional oscillatory force about its axis of oscillation;

(5) means for measuring the amplitude of the resulting torsional oscillation of the supporting means; and (6) means for measuring either (i) the angular phase difference between the oscillations of the supporting means and those of the oscillation-generating means, in a case where the latter oscillations are of fixed, predetermined frequency, or (ii) the frequency of the oscillations of the generating means, in a case where that frequency is adjusted to the resonant frequency of the combination of the vessel, the sample and the supporting means in conjunction with the elastic coupling.

In a preferred embodiment of the method of the invention, the source of oscillation is operated at a fixed, predetermined frequency, and measurements are made of the amplitude of the resulting oscillations of the vessel and sample and also of the angular phase difference between those oscillations and those of the source. Correspondingly, in a preferred form of the apparatus of the invention, the oscillation-generating means operates at a fixed, predetermined frequency and the apparatus incorporates means for measuring the amplitude of the resulting oscillations of the vessel and sample and means for measuring the angular phase difference between those oscillations and those of the generating means.

The invention can, however, be performed in the alternative embodiment where the frequency of the source of oscillation is adjusted to coincide with the natural resonant frequency of the combination of the vessel, the sample and the supporting means, in conjunction with the elastic coupling, and the measurements taken are then of the amplitude and frequency of the resulting oscillations of the vessel and sample. In the apparatus used for this alternative method, it may be arranged either that the frequency of the oscillation-generating means is adjustable manually so that it can be made to coincide with the aforesaid resonant frequency, or that it is adjusted automatically by means of positive feedback between the vessel-supporting means and the oscillation-generating means so as to coincide with that frequency.

As already stated, the vessel within which the sample of liquid is contained has the form of a solid of revolution; thus it may take various shapes, such as a sphere or part thereof, a cone or a frustum of a cone, or more complex shapes. However, the simplest and commonly most suitable form of vessel is a hollow cylinder.

By "means for elastically coupling the supporting means to the oscillation-generating means" we refer principally to some form of spring interconnecting the two components in question, but we also include a coupling of the magnetic type in which there is no mechanical interconnection between the two components.

In order to explain the nature of the invention more fully, a description follows, by way of example, of a method and apparatus according to the preferred embodiment of the invention as discussed above. The apparatus in question is suitable for carrying out measurements upon liquids as hereinbefore defined contained in cylindrical vessels having a nominal volume of 0.5 liter, and operates at a fixed frequency of oscillation of 10 Hz.

The mechanical parts of the apparatus are shown schematically in the accompanying FIG. 1.

FIGS. 3 and 4 are calibration graphs.

Figure 1:
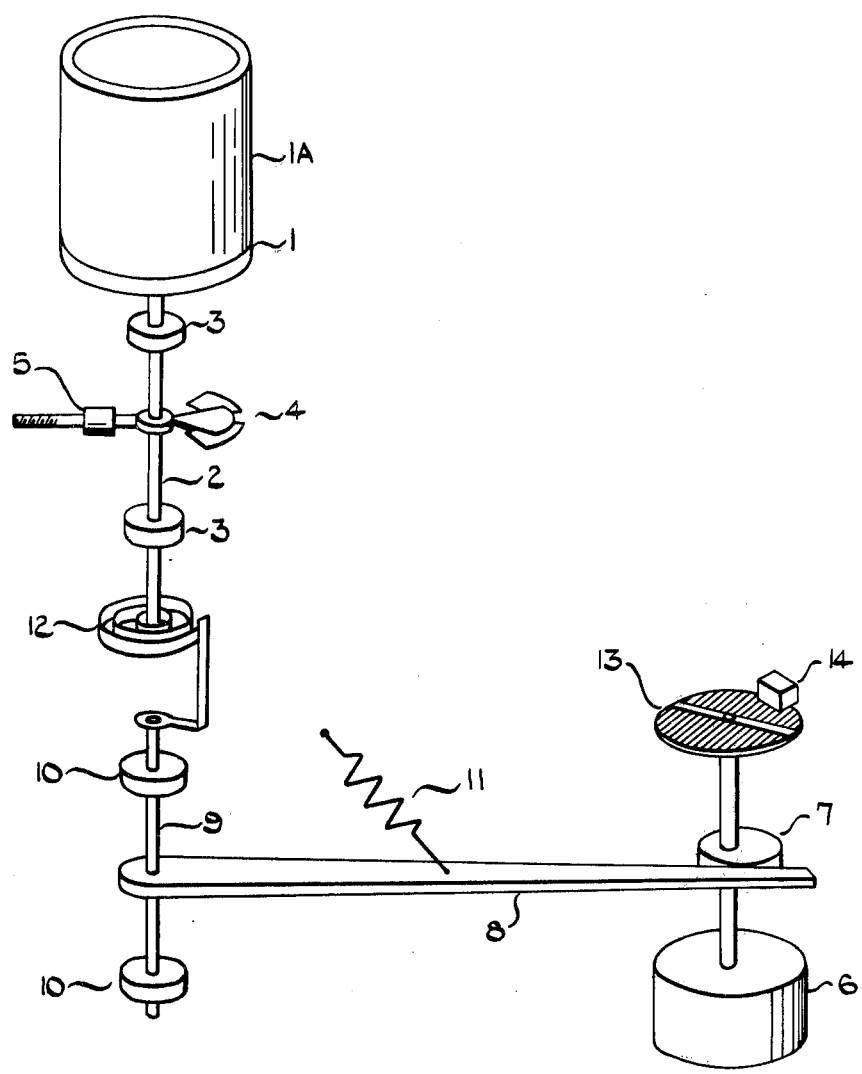

A horizontal turntable 1 (FIG. 1) is mounted upon a vertical shaft 2 which is supported in low-friction ball bearings 3. The shaft 2 carries the moving blade of a variable differential capacitor 4, and also a threaded rod carrying an adjustable counter-mass 5 whereby the moment of inertia of the turntable assembly can be varied. The turntable 1 supports a cylindrical container 1A, such as a metal can, in which the liquid to be tested is held; the upper surface of the turntable is contoured so as to locate the cylindrical container in a position where its axis of symmetry coincides with the vertical axis of the turntable; the weight of the container and contents is normally adequate to ensure that no motion of the container occurs relative to that of the turntable. A mechanical oscillator comprises a synchronous motor 6 which rotates a shaft, carrying an eccentrically mounted circular cam 7, at 10 revolutions per second. An arm 8 is mounted at one end upon a shaft 9 which is carried in ball bearings 10; a spring 11 urges the other end of the arm continuously in contact with the cam 7. The two shafts 2 and 9 are co-axially mounted and are coupled to each other by means of a spiral spring 12. The strength of the spring 12 is such that, when an empty container, identical with that in which the liquid is to be tested, is placed on the turntable 1, the natural frequency of oscillation of the turntable assembly together with the container under the action of the coupling spring is equal to or near the chosen frequency of operation at 10 Hz. By fine adjustment of the position of the counter-mass 5, the combination of the turntable assembly and empty container is brought exactly into resonance at that frequency. The dimensions of the cam 7 and the arm 8 are chosen so that the angular amplitude of the resulting oscillations of the shaft 9 is about 0.25° peak to peak. Also mounted upon the shaft carrying the cam 7 is a thin disc 13, the face of which is painted black except for two narrow segments symmetrically disposed about a diameter of the disc and coloured white. A sensing device 14 is placed in proximity to the coloured face of the disc 13. This device consists of a light-emitting diode and a phototransistor in combination, whereby at every half rotation of the disc 13, and hence of the cam 7, an electrical pulse is generated (means, not shown, are provided for adjusting the angular position of the disc 13 relative to that of the shaft on which it is carried).

Figure 2:
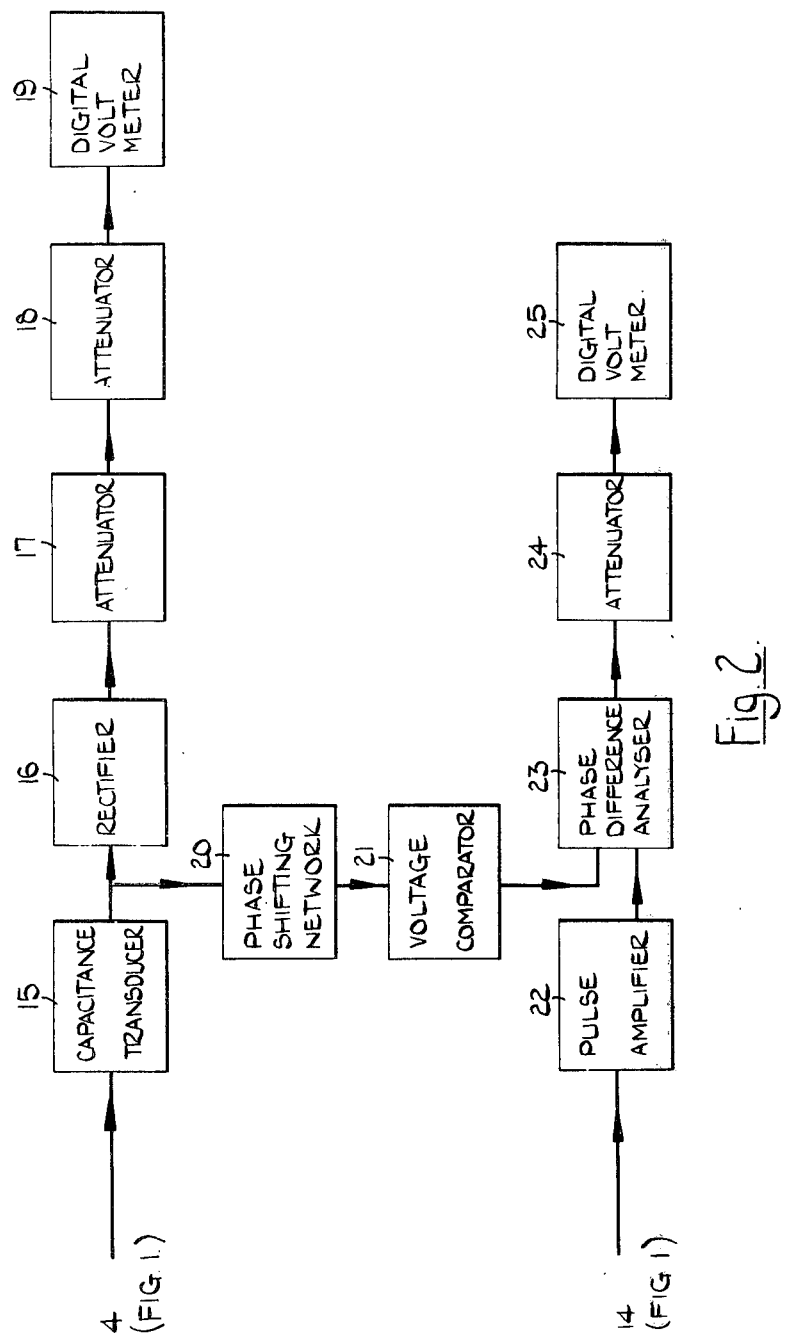
FIG. 2 is a block diagram of the associated electrical measuring circuits.

Referring now to FIG. 2, it will be seen that the differential variable capacitor 4 is linked to a capacitance transducer 15 whereby an electrical output is obtained which is proportional to the displacement of the turntable 1 from its mean position. This output is rectified and smoothed by the unit 16 to give a steady output which is proportional to the amplitude of oscillation of the turntable. This last output is attenuated in two stages by attenuators 17 and 18, and finally is displayed on a digital voltmeter 19. Attenuator 17 is used to adjust the level of the output so that the display reads in convenient units of amplitude. Attenuator 18 is also adjustable and carries a dial calibrated in units of mass, so that the system can be compensated for variations in mass from one sample being tested to another. The electrical output from the transducer 15 is also applied to a phase-shifting network 20 and a voltage comparator 21, in such a manner that an electrical pulse is generated every time the turntable 1 passes through its mean position. The electrical pulses from the photoelectric device 14 are passed through an amplifier 22 and are then compared with the pulses from the voltage comparator 21 by the phase-difference analyser 23, which generates a steady electrical output proportional in magnitude to the phase difference between the oscillations of the turntable and those of the drive shaft 9 (this arrangement cannot in fact distinguish between an angular phase difference of $\Delta°$ and one of $(180+\Delta)°$, but in the present case this is of no consequence since $\Delta$ always lies between 90° and 180°). The output from the analyser 23 is attenuated by an attenuator 24 and is displayed on a second digital voltmeter 25; the attenuator 24 can be adjusted so that the display reads in convenient units of phase difference. The purpose of the phase-shifting network 20 is to compensate for various incidental phase shifts that occur in the electronic circuits and those that are the result of inexact positioning of the rotating disc 13.

The synchronous motor 6 is preferably supplied with power from a 50 Hz alternating current supply generated by frequency division and power amplification from a 100 KHz crystal-controlled oscillator. If the motor is operated from the ordinary domestic 50 Hz electricity supply, there is a risk of frequency fluctuations introducing errors into the measurements made with the apparatus.

The apparatus is used in the following manner. The sample, of previously ascertained mass and contained within a can or other cylindrical container, is placed on the turntable 1, the calibration dial of attenuator 18 is adjusted according to the mass of the sample (the mass of the container is not included) and the readings of the parameters representing the amplitude and the phase difference of the oscillations of the turntable are read off from the digital voltmeters 19 and 25 respectively.

As already indicated, the method and apparatus of the invention can be used simply for an empirical comparison of the viscoelastic characteristics of one sample of a liquid against those of another, for example those of a standard material. In these circumstances, the numerical values of the voltages read off from the two digital voltmeters may be used directly as the basis of comparison. However, these readings may also be employed to derive a measure of the actual viscoelastic moduli of a sample, without reference to any standard liquid, by virtue of the theoretical analysis which follows.

It is believed that a complete theoretical analysis has not previously been made of the relationship between the motion of a viscoelastic liquid in circumstances such as those of a sample under test as described above, and the viscoelastic properties of the liquid. For the present purposes, therefore, an extension has been worked out of the analysis made for inelastic liquids and an apparatus of a different kind by M. R. Hopkins and T. C. Toye in Proc. Phys. Soc. B. 63, 773 (1950).

The relationship between the motion of a viscoelastic material in a container that is oscillating sinusoidally about an axis of symmetry, and the viscoelastic moduli of the material can be deduced by well-known methods of differential calculus by considering the forces on an elementary volume of the sample material. For an infinitesimal volume of the material having the cylindrical polar co-ordinates (r, $\theta$, z), the polar axis being vertical and coincident with the axis of symmetry of the container, r being measured perpendicularly to that axis and z being measured upwards in a direction parallel to that axis, the co-ordinates (0, 0, 0) referring to the centre of the base of the container, the motion of the material is described by the partial differential equation:

$$\frac{\partial^2 \phi}{\partial r^2} + \frac{3}{r} \frac{\partial \phi}{\partial r} + \frac{\partial^2 \phi}{\partial z^2} + m^2 \phi = 0 \quad (1)$$

where $\phi$, which is a function of r and z alone, is defined by the relationship $$\theta = \phi e^{ipt}$$

and where $$m^2 = p^2 \rho / G^*$$

in which $$G^* = G' + iG'' = G' + ip \, \eta'.$$

Other symbols used above have the following meaning:
(i) p is the periodicity of the oscillation ($=2\pi \times$ frequency of oscillation)
(ii) $\rho$ is the density of the sample material;
(iii) t is the co-ordinate of time;
(iv) G* is the complex viscoelastic shear modulus of the sample material;
(v) G' is the shear storage modulus;
(vi) G" is the shear loss modulus;
(vii) $\eta'$ is the real part of complex viscosity;
(viii) i is $(-1)^{\frac{1}{2}}$ The significance of the viscoelastic quantities G*, G', G", and $\eta'$ is described in the literature, for example, in "Viscoelastic Properties of Polymers" by J. D. Ferry, published by John Wiley and Sons Inc., (1961). Mathematical solution of equation (1) to suit the specific shape of container chosen allows the torsional force exerted by the sample material on its oscillating container to be calculated. For a cylindrical container of radius R filled to a height H, oscillating sinusoidally with a periodicity p, the torsional force exerted by the material on the container is given by the expression:

$$2\pi G^* \left[ -\frac{mHR^3 J_2(mR)}{J_1(mR)} + 2m^4 R^2 \sum_{n=1}^{\infty} \frac{\tanh(l_n H)}{l_n^3 k_n^2} \right] \theta' \quad (2)$$

where
$J_1$ and $J_2$ are Bessel functions of order 1 and 2 respectively
the summation $\Sigma$ is taken over the positive roots $k_n$ of $J_1(k_n R) = 0$, $l_n^2 = k_n^2 - m^2$, and
$\theta'$ is the angular deflection of the container from the mid-point of oscillation (all other symbols have the same meaning as in equation (1)). The sample is assumed to have a free upper surface.

The motion of the turntable of an apparatus of the kind hereinabove described, for the case of a viscoelastic sample in a cylindrical container, can be calculated by well-known methods from expression (2) above. The equation describing this motion is as follows:

$$\frac{\theta_o}{\theta_{sample}} \cdot e^{i\Delta} = \frac{2MR^2 p^2}{k_s} \left( -\frac{1}{mR} \cdot \frac{J_2(mR)}{J_1(mR)} + \frac{2m^2}{R^2 H} \sum_{n=1}^{\infty} \frac{\tanh(l_n H)}{l_n^3 k_n^2} \right) - \frac{p^2 I}{k_s} + 1 \quad (3)$$

where the symbols have the same meaning as before except that the additional symbols have the following meanings:
$\theta_o$ is the angular amplitude of oscillation of the mechanical oscillator;
$\theta_{sample}$ is the angular amplitude of oscillation of the turntable;
$\Delta$ is the phase difference between the oscillation of the turntable and that of the mechanical oscillator;
$k_s$ is the torque required to turn the turntable by unit angle against the action of the coupling spring;
I is the combined moment of inertia of the turntable assembly and a container of appropriate size about the axis of rotation;
M is the mass of the sample with container excluded.

From the foregoing analysis, it is possible to proceed to the preparation of calibration graphs or other means whereby the viscoelastic parameters may be quickly derived from the numerical quantities read off from the two digital voltmeters of the apparatus described in detail above. In respect of that apparatus, some simplification of the mathematical analysis arises from the fact that the mechanical oscillator there operates at a fixed, predetermined frequency, with which the turntable assembly together with an empty container is in resonance under the action of the coupling spring. This simplification is, namely, that under these conditions the expression $(-p^2 I/k_s + 1)$ in equation (3) above is equal to zero. A further modification of practical convenience is to measure the amplitude $\theta_{sample}$ in terms of the amplitude of oscillation of a solid calibration standard, $\theta_{solid}$, rather than that of the mechanical oscillator, $\theta_o$. A convenient solid calibration standard consists of a container identical with those used for the samples which are to be measured, containing solid material numerically equal in mass to the nominal volume of the container. The term "solid" in this context means a material which is not deformed significantly by the oscillatory motion of the container, but assumes that the material has been made to conform to the shape of the container as though it were a liquid. Alternatively, the solid calibration standard can be made of any convenient solid material provided it has exactly the same moment of inertia about the axis of rotation as the solid calibration standard defined above. The amplitude of oscillation of the solid calibration standard, for the case where $-p^2I/k_s+1=0$, is given by the following equation:

$$\theta_o/\theta_{solid} = M'R^2p^2/2k_s \qquad \ldots (4)$$

where M' is the mass of solid material in the solid calibration standard first described above.

For most practical applications of the invention, it is preferred to calculate two parameters $\alpha$ and $\beta$ rather than the viscoelastic moduli $G^*$, $G'$, $G''$, or $\eta'$. The quantities $\alpha$ and $\beta$ are defined as follows:

$$\alpha = \left[\left(\frac{G'}{p\rho}\right)^2 + \left(\frac{\eta'}{\rho}\right)^2\right]^{\frac{1}{2}}, \beta = \frac{G'}{p\eta'} \qquad (5)$$

The use of $\alpha$ and $\beta$ gives calibration graphs of more convenient shape, and is of greater practical significance in most cases. $\alpha$ may be regarded as the kinetic viscoelastic impedance (by analogy with electrical impedance); $\beta$ is commonly known as tan $\delta$ in the theory of viscoelasticity.

Combination of equations (3) and (4) gives, again for the case where $-p^2I/k_s+1=0$, the following expression:

$$\frac{\theta_{solid}}{\theta_{sample}} \cdot e^{i\Delta} = \frac{4M}{M'}\left(-\frac{1}{mR} \cdot \frac{J_2(mR)}{J_1(mR)} + \frac{2m^2}{R^2H} \sum_{n=1}^{\infty} \frac{\tanh(l_nH)}{l_n^3K_n^2}\right) \qquad (6)$$

If equation (6) is rewritten in the form $$1/A \, e^{i\Delta} = 4M/M'(C+iD) \qquad \ldots (6a)$$

then $$A = M'/4M \, (C^2+D^2)^{-\frac{1}{2}} \qquad \ldots (7)$$

and $$\Delta = \arctan D/C, \qquad \ldots (8)$$

where A is the amplitude of oscillation of the sample as a proportion of that of the solid calibration standard and $\Delta$ is the phase difference between the oscillation of the turntable and that of the mechanical oscillator, as before. The advantage of this procedure is that it provides a convenient way of calibrating the amplitude scale, does not require a knowledge of either the spring constant $k_s$ or the mechanical oscillator amplitude $\theta_o$, and the appropriate calibration graphs apply to any apparatus having the same frequency of oscillation, and using the same size and shape of container.

Figure 3:
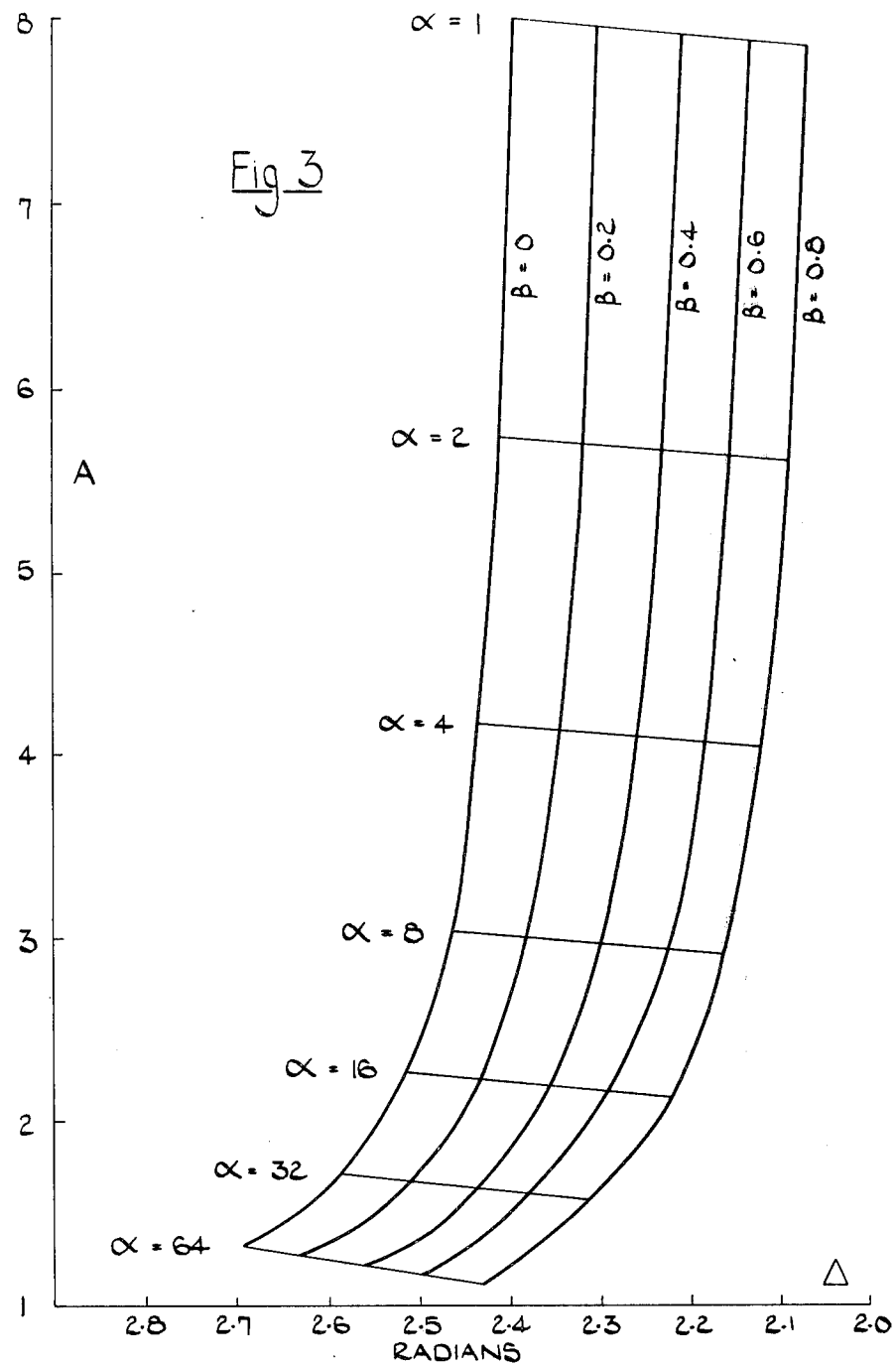

An illustration is given in FIG. 3 of a calibration graph which is constructed in accordance with equations (6), (6a), (7) and (8) and is suitable for converting measurements of the quantities A and $\Delta$ made upon samples of 0.5 l nominal volume by means of the apparatus described above. The graph is constructed by substituting selected specific values of the viscoelastic parameters $\alpha$ and $\beta$ in the equations and thence computing the corresponding values of A and $\Delta$. In practice, the quantity A is read off directly from the digital voltmeter 19, the attenuator 17 having been suitably adjusted for the solid calibration standard, and the quantity $\Delta$ is likewise read off from the digital voltmeter 25. The position is then found on the graph of the point which has the co-ordinates A and $\Delta$ as determined and the corresponding values of the viscoelastic parameters $\alpha$ and $\beta$ are then estimated by interpolation from the family of curves inscribed on the graph.

The method and apparatus of the invention as described in detail above can be adapted for the measurement of the characteristics of a wide range of sizes of samples and containers. Although the constructional details of an apparatus designed to operate with samples weighing many kilograms may differ from those of the apparatus described above, the underlying principles will remain the same. The fixed frequency at which the sample is oscillated will require to be chosen so as to provide a suitable range of measurement for the size of samples contemplated; the choice can be made on the basis either of simple experimentation or of theoretical analysis. Again, the angular amplitude of the mechanical oscillator is selected so as to be large enough to give amplitudes of oscillation of the turntable and sample which are convenient for accurate measurement, but not so large that the rheological nature of the sample may be altered by the motion imparted to it. The strength of the spring or other elastic coupling between the mechanical oscillator and the turntable is chosen so that, when an empty container is placed on the turntable, the natural frequency of oscillation of the turntable assembly together with the container under the action of the coupling spring is equal to or near the already selected frequency of operation. As already indicated, any final exact adjustment of that natural frequency which is necessary, in order to bring the turntable and empty container into resonance with the mechanical oscillator, can be made by slightly altering the moment of inertia of the turntable assembly.

Other suitable modifications of the apparatus as described will be apparent to those skilled in the art. For example, instead of a spiral spring as illustrated, a spring of any other convenient shape, for example a leaf spring, may be used, or, as previously mentioned, the coupling may be of the magnetic type in which there is no actual mechanical connection between the two members to be coupled. The mechanical oscillator does not necessarily have to produce an oscillation of sinusoidal wave form, as is the case with the construction illustrated above; other forms of oscillation, such as square waves or pulses of short duration, may be used provided they have the required frequency of repetition. Thus the cam 7 shown in FIG. 1 may be replaced by a suitable magnetic solenoid driven by an intermittent electrical current having a repetition frequency of 10 Hz, the timing pulses generated by the device 14 being then replaced by pulses derived directly from the said intermittent electric current. The digital voltmeters 19 and 25 can, of course, be replaced by conventional voltmeters giving scale readings.

It will be appreciated that the method and apparatus of the invention are well suited to routine measurements of viscoelastic characteristics, for example as a quality control of material in manufacture, or as a check upon the storage stability of a material after manufacture. The containers in which the samples are placed may be either open or closed during measurement, and the apparatus can therefore be designed so as to operate with materials as packaged ready for sale, provided that the containers are of the type hereinbefore defined. Above all, the method and apparatus are suitable in relation to viscoelastic products which are commonly packaged in cylindrical tins or cans, such as paints, food products such as jellies, blancmanges and soups, cosmetic products such as face creams, and products of the oil industry.

In the alternative embodiment of the invention, where the oscillation-generating means is adjusted to operate at the resonant frequency of the combination of the vessel, the sample and the supporting means in conjunction with the elastic coupling, the construction of the apparatus will be modified as compared with the version described in detail above. The modifications required will, however, be readily apparent to those skilled in the art and the underlying principles of operation will remain the same as those already described; in particular, equation (3) will still be applicable for the case of a cylindrical container. As an example of such a modification, there may be mentioned the provision of a manual control whereby the frequency of the mechanical oscillator can be varied until the value is found at which the amplitude of the oscillations of the vessel and sample attains a maximum. For an empirical comparison of a sample liquid against a standard liquid, the actual measured values of amplitude and frequency will suffice. The derivation of viscoelastic moduli, or related parameters, from those values can be achieved by straightforward modification of the theoretical analysis given above.

In all the foregoing description, it has been assumed that the sample liquid is homogeneous, but it is possible to utilise the method and apparatus of the invention to investigate samples which are subject to settlement on storage so that a uniform solid layer builds up upon the bottom of the container. Provided that the flow properties of the supernatant material are essentially Newtonian, data obtained from measurements carried out as previously described can be used to calculate the proportion of the contents of the container which is present as a hard settlement and also the kinematic viscosity of the supernatant material.

It can be shown that $$\frac{1}{A^2} = \frac{(1-x)^2}{A_o^2} - \frac{2 \times (1-x)}{A_o} \cos \Delta_o + x^2 \quad (9)$$

and $$\tan \Delta = \frac{\sin \Delta_o}{\cos \Delta_o - A_o \times /(1-x)} \quad (10)$$

where $A_o$ and $A$ are the A-values of the sample measured before and after settlement has occurred respectively, $\Delta_o$ and $\Delta$ are the corresponding $\Delta$-values, and x is the mass fraction of the sample which has settled out.

From these two equations (9) and (10), a family of graphs can be constructed which can be superimposed on the previously described calibration graph, as illustrated in FIG. 4 for a 250 ml. nominal sample volume at an operational frequency of 9.77 Hz. It will be seen that the "settlement" graphs lie in an area which is not accessible to homogeneous samples and it is this characteristic which is utilised to recognise that settlement has occurred. In straightforward cases, the A, $\Delta$ values for the sample will be initially on the curve $\beta = 0$, and then, as settlement proceeds, will move steadily in a direction nearly parallel with the nearest theoretical settlement line corresponding to a constant value of x. The proportion of settlement can thus be estimated by reference to the theoretical lines of constant x value.

We claim:

1. A method of measuring viscoelastic characteristics of a sample of a viscous liquid like material while the sample is contained within a hollow vessel the walls of which describe a solid of revolution about the axis of symmetry of the vessel, the method comprising:

(a) supporting the vessel and sample and subjecting them to torsional oscillation about a vertical axis coinciding with the axis of symmetry of the vessel, the torsional oscillation being imparted to the vessel through an elastic coupling by a source of oscillation which is either of fixed, predetermined frequency or is adjusted to the resonant frequency of the vessel, its support and the sample in conjunction with the elastic coupling;

(b) measuring the amplitude of the resulting oscillation of the vessel and also measuring the angular phase difference between the oscillations of the vessel and those of the source; and (c) comparing the measured values for the sample with the corresponding known values for a standard liquid like material, or deriving viscoelastic moduli, or parameters related thereto, from the measured values for the sample by means of mathematical formulae or by means of calibration graphs or tables prepared with the aid of such formulae.

2. An apparatus suitable for the measurement of the viscoelastic characteristics of a sample of viscous liquid like material, which sample is contained within a hollow vessel the walls of which describe a solid of revolution about the axis of symmetry of the vessel, the apparatus comprising the following components:

(1) means for supporting the vessel so that its axis of symmetry is vertical, the said means being mounted for low-friction oscillation about a vertical axis passing through its centre but being constrained from moving in any other mode;

(2) means attached to the supporting means for locating thereupon a said hollow vessel containing the sample so that the axis of symmetry of the vessel coincides with the vertical axis of the supporting means and so that the vessel does not move relatively to the supporting means during oscillation thereof;

(3) means for generating a mechanical oscillation of either fixed, predetermined frequency or of adjustable frequency;

(4) means for elastically coupling the supporting means to the oscillation-generating means so that the supporting means is subjected in response thereto to a torsional oscillatory force about its axis of oscillation;

(5) means for measuring the amplitude of the resulting torsional oscillation of the supporting means; and (6) means for measuring the angular phase difference between the oscillations of the supporting means and those of the oscillation-generating means.

3. An apparatus as claimed in claim 2, wherein the vessel within which the sample is contained is a hollow cylinder.

4. An apparatus as claimed in claim 2, wherein the frequency of the oscillation-generating means is adjusted automatically by means of positive feedback between the vessel-supporting means and the oscillation-generating means so as to cause the said frequency to coincide with the resonant frequency of the combination of the vessel, the sample and the supporting means in conjunction with the elastic coupling.

5. An apparatus as claimed in claim 2, wherein the means for elastically coupling the supporting means to the oscillation-generating means is a spring.

6. An apparatus as claimed in claim 2, wherein the means for measuring the amplitude of oscillation of the supporting means comprises a variable differential capacitor the moving blade of which is mechanically connected to the supporting means and which is linked to a capacitance transducer whereby an electrical output is obtained which is proportional to the displacement of the supporting means from its mean position.

7. An apparatus as claimed in claim 6, wherein the means for measuring the angular phase difference between the oscillations of the supporting means and the oscillations of the oscillation-generating means comprises (i) a phase-shifting network and a voltage comparator to which the electrical output from the capacitance transducer is applied so as to generate an electrical pulse every time the supporting means passes through its mean position (ii) means for generating an electrical pulse at intervals equal to the interval between each half-cycle of the oscillation-generating means; (iii) a phase-difference analyser for comparing the pulses from (i) with the pulses from (ii) and thence generating a steady electrical output proportional in magnitude to the phase difference between those pulses.

8. A method of measuring viscoelastic characteristics of a sample of a viscous liquid-like material, while the sample is contained within a hollow vessel the walls of which describe a solid of revolution about the axis of symmetry of the vessel, the method comprising:

(a) supporting the vessel and sample and subjecting them to torsional oscillation about a vertical axis coinciding with the axis of symmetry of the vessel, the torsional oscillation being imparted to the vessel through an elastic coupling by a source of oscillation which is either of fixed, predetermined frequency or is adjusted to the resonant frequency of the vessel, its support and the sample in conjunction with the elastic coupling;

(b) measuring the amplitude of the resulting oscillation of the vessel and also measuring the resonant frequency of the vessel and sample, the source being adjusted to that frequency; and (c) comparing the measured values for the sample with the corresponding known values for a standard liquid-like material, or deriving viscoelastic moduli, or parameters related thereto, from the measured values for the sample by means of mathematical formulae or by means of calibration graphs or tables prepared with the aid of such formulae.

9. An apparatus suitable for the measurement of the viscoelastic characteristics of a sample of viscous liquid-like material, which sample is contained within a hollow vessel the walls of which describe a solid of revolution about the axis of symmetry of the vessel, the apparatus comprising the following components:

(a) means for supporting the vessel so that its axis of symmetry is vertical, the said means being mounted for low-friction oscillation about a vertical axis passing through its center but being constrained from moving in any other mode;

(b) means attached to the supporting means for locating therupon a said hollow vessel containing the sample so that the axis of symmetry of the vessel coincides with the vertical axis of the supporting means and so that the vessel does not move relatively to the supporting means during oscillation thereof;

(c) means for generating a mechanical oscillation of either fixed, predetermined frequency or of adjustable frequency;

(d) means for elastically coupling the supporting means to the oscillation-generating means so that the supporting means is subjected in response thereto to a torsional oscillatory force about its axis of oscillation;

(e) means for measuring the amplitude of the resulting torsional oscillation of the supporting means; and (f) means for measuring the frequency of the oscillations of the generating means, that frequency being adjusted to the resonant frequency to the combination of the vessel, the sample and the supporting means in conjunction with the elastic coupling.

* * * * *